Figure 1:
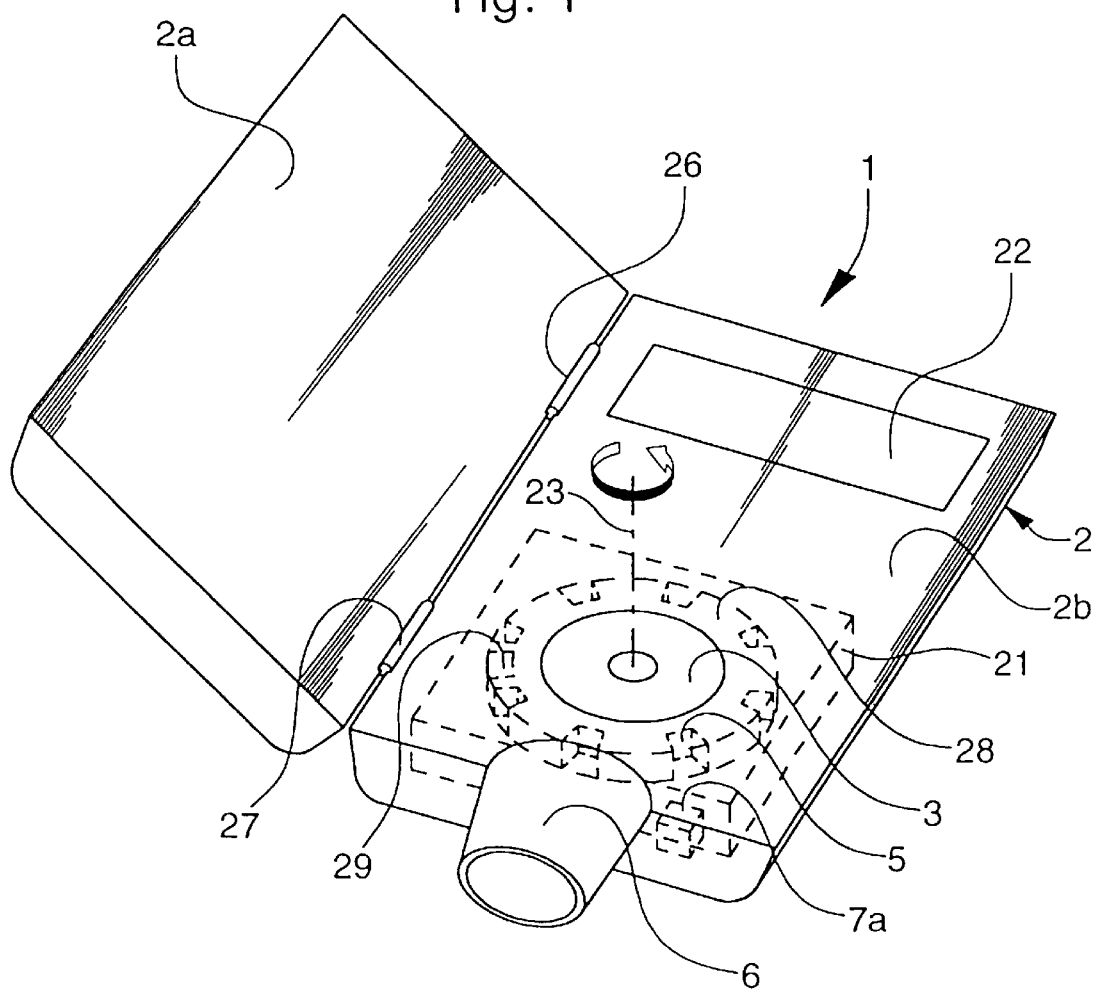

US006196219B1

(12) United States Patent
Hess et al.

(10) Patent No.: US 6,196,219 B1
(45) Date of Patent: Mar. 6, 2001

(54) LIQUID DROPLET SPRAY DEVICE FOR AN INHALER SUITABLE FOR RESPIRATORY THERAPIES

(75) Inventors: Joseph Hess, Bevaix; Hu Bo, Peseux; Raphaël Weber, La Chaux-de-Fonds; Isabel Ortega, Le Locle; Cédric Barraud, Cornaux; Bart van der Schoot, Neuchâtel; Nicolaas Frans de Rooij, Bôle; Bas de Heij, Neuchâtel, all of (CH)

(73) Assignee: Microflow Engineering SA, Neuchatel (CH)

( * ) Notice: Subject to any disclaimer, the term of this patent is extended or adjusted under 35 U.S.C. 154(b) by 0 days.

(21) Appl. No.: 09/195,699

(22) Filed: Nov. 19, 1998

(30) Foreign Application Priority Data

Nov. 19, 1997 (EP) ........................................ 97120287
Jun. 23, 1998 (EP) ........................................ 98111497

(51) Int. Cl.[7] ........................................ A61M 11/00
(52) U.S. Cl. ........................ 128/200.21; 128/200.14; 239/102.2
(58) Field of Search ..................... 128/200.14, 200.15, 128/200.21, 203.12, 203.27, 203.26; 239/102.2

(56) References Cited

U.S. PATENT DOCUMENTS

| | | | | |
|---|---|---|---|---|
| 3,828,773 | | 8/1974 | Buch et al. . | |
| 4,790,479 | * | 12/1988 | Matsumoto et al. | 128/200.16 |
| 5,063,921 | * | 11/1991 | Howe | 128/203.26 |
| 5,487,378 | * | 1/1996 | Robertson et al. | 128/200.16 |
| 5,497,763 | | 3/1996 | Lloyd et al. . | |
| 5,586,550 | * | 12/1996 | Ivri et al. | 128/200.14 |
| 5,660,167 | * | 8/1997 | Ryder | 128/200.14 |
| 5,842,468 | * | 12/1998 | Denyer et al. | 128/200.14 |
| 5,950,619 | * | 9/1999 | Van Der Linden et al. | 128/200.14 |

FOREIGN PATENT DOCUMENTS

| | | |
|---|---|---|
| 0 516 565 B1 | 4/1996 | (EP) . |
| WO 90/01997 | 3/1990 | (WO) . |
| WO 92/11050 | 7/1992 | (WO) . |
| WO 95/15822 | 6/1995 | (WO) . |

* cited by examiner

*Primary Examiner*—John G. Weiss
(74) *Attorney, Agent, or Firm*—Griffin & Szipl, P.C.

(57) ABSTRACT

The liquid droplet spray device (5) has a micromachined substrate (8, 18, 18*a*; 8*a*, 18, 18*a*), a space (9) within the substrate for containing a liquid substance (4), an inlet channel for supplying (7) the liquid (4) to the space (9), and outlet structure (13, 14, 15) for ejecting the liquid as a mono-dispersive droplet spray when the liquid undergoes a vibration. The outlet structure comprises a cut-off pyramid-shaped tapered cavity (13) which is micromachined in the space (9). The outlet structure further comprises at least one output (14) and output channel (15) connecting the tapered cavity (13) to the outlet (14), the outlet (14) and the output channel (15) having a non-tapered vertical shape. Thanks to such a device, the exact amount ejected may be determined accurately which allows for a predicted lung deposition of the droplets by using appropriate control means adapted to the kind of patient.

27 Claims, 4 Drawing Sheets

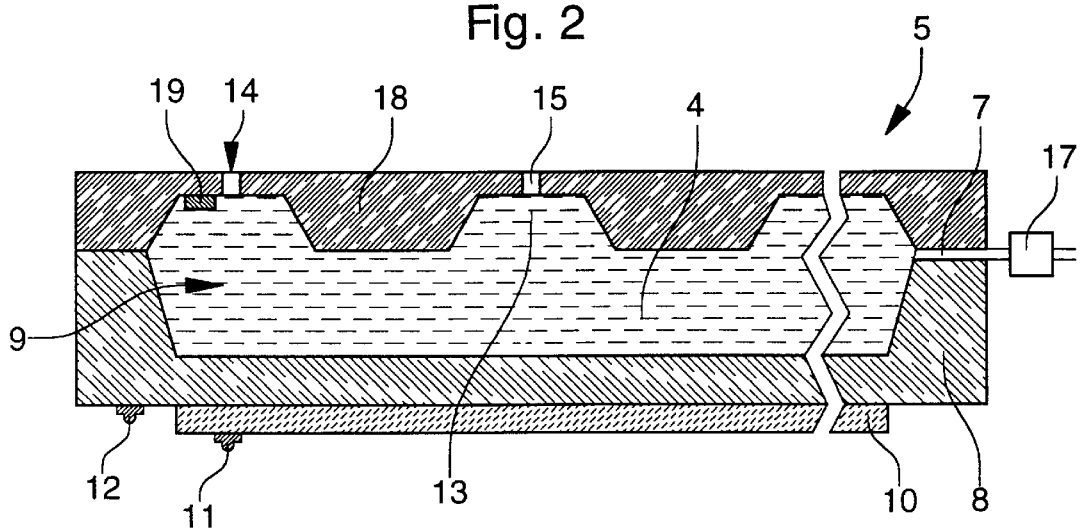
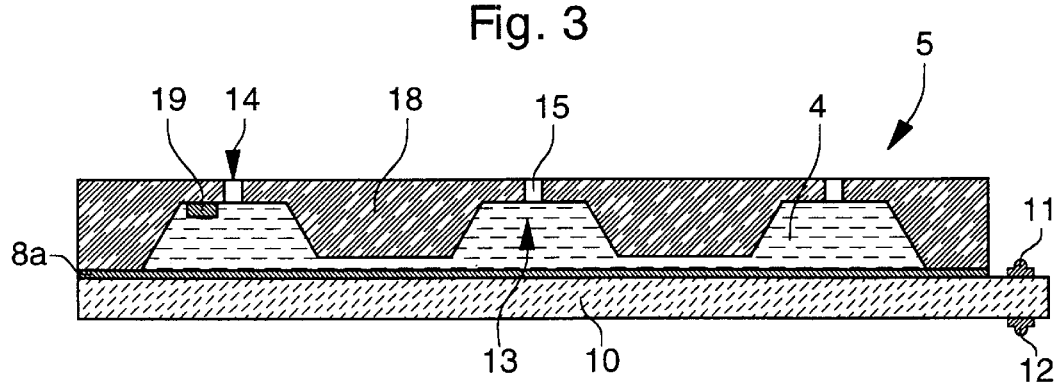
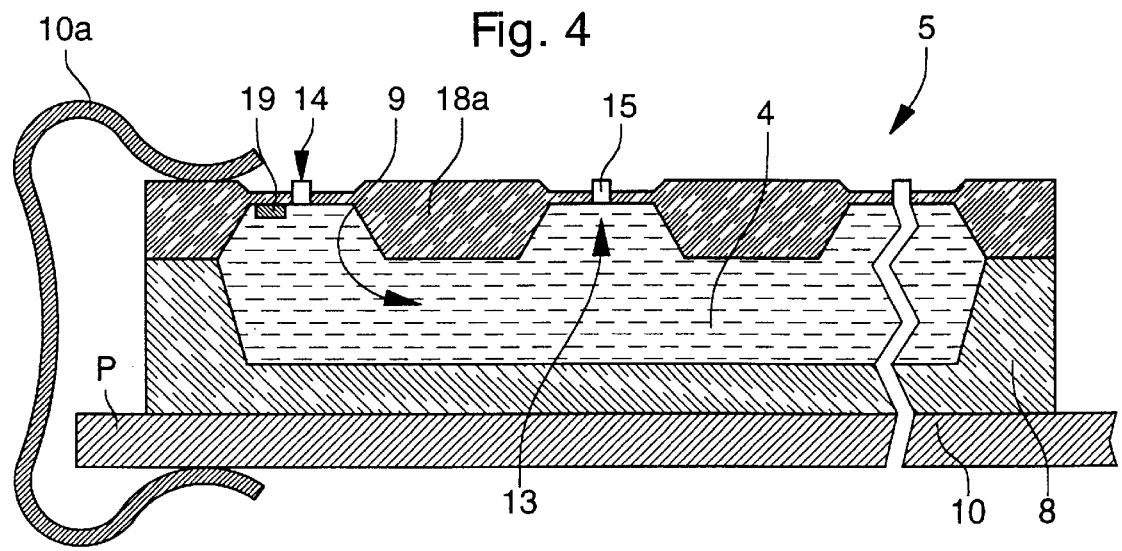

LIQUID DROPLET SPRAY DEVICE FOR AN INHALER SUITABLE FOR RESPIRATORY THERAPIES

The present invention relates generally to drug administration devices, and in particular to a device for administrating a drug to a patient by means of his or her respiratory system. Such an inhalation device, in its simplest form, is commonly called an inhaler. It may be used e.g. for the controlled administration of drugs or for a variety of therapies using aerosolised drug administration including anaesthetics. The inhaler delivers the drug, which is in the form of a liquid substance, as a dispersion of atomised droplets. Preferably, such a device is small in size and battery operated so that the patient may carry and use it in a discreet manner. Preferably also the device is made in such a way that it is possible to use the same device for administrating more than one drug and to distinguish one drug from another. More specifically, the present invention concerns the liquid droplet spray device which creates the droplet spray of the inhaler or aerosolised drug delivery system and its control means.

Various devices are known for atomising a liquid. Document EP 0 516 565 describes am ultrasonic wave nebuliser which atomises water. This apparatus is used as a room humidifier. Vibration is transmitted through the water to the water surface from which the spray is produced. A perforate membrane is provided to retain the water in absence of oscillation. Such devices are particularly ineffective in vaporising suspensions as explained in the Research Article "Comparison of a respiratory suspension aerosolised by an air-jet and an ultrasonic nebuliser" by Susan L. Tiano and Richard N. Dalby in Pharmaceutical Development and Technology, I(3), 261–268 (1996). Typically, inhaler devices do use the same principle to atomise the liquid into droplets, see for example the document WO 95/15822.

However, the droplet size does not only depend on the size of the outlet orifices of the perforate membrane, but is also dependent on the vibration frequency. In order to obtain a small droplet, a very high frequency must be used, typically over 1 MHz for droplets of about 10 $\mu$m in diameter. This leads to an increased power consumption due to the high frequency so that such a device is not suitable for a small battery operated device. Furthermore, the exact size of the droplet is not always constant due to frequency response fluctuations with temperature and to membrane fabrication tolerances.

As is generally known, the efficacy of a drug therapy treatment depends on the substance's activity, which depends on the composition, on the place of impact, i.e. the place at which it may carry out its activity, and on the dose repeatability, i.e. the fact that the volume of each dose ejected remains constant.

With a large variation of droplet size, it is almost impossible to determine the quantity and where exactly the droplets will arrive. In fact, the liquid atomised by the inhaler is to reach certain parts of the lungs to have a maximum effect dependant on the therapy. It is thus desirable to be able to determine or to "target" the impact or deposition position of the droplets to obtain an efficient therapy.

Further, the orifices can not be made too small, not only because of fabrication reasons, but also in order to avoid clogging of the outlet orifices by the substance. In fact, it is known that the aqueous solubility of the substance solution depends on the composition of the drugs used and on its temperature. It is also known that such orifices might be clogged by very small amounts of drug left in the liquid spray device after atomisation.

To ensure that a certain amount of substance is indeed released, it has been proposed to monitor the amount of liquid released when the inhaler is used. The document WO 92/11050 describes such an inhaler having means for cyclically pressurising the liquid such that the liquid is periodically expelled and also having control means for deactivating the droplet generator after a predetermined time, e.g. by using a timer, or after a predetermined volume of liquid has been expelled. However, this document is completely silent about droplet size control, aqueous solution or suspension characteristics as well as about any deposition target determination and control of the liquid.

Another prior art device is known from the document U.S. Pat. No. 5,497,763. This device has a breath actuated release of aerosolised drug and has a porous membrane located above a dosage unit container. The pores are preferably cone-shaped to reduce the force needed to move the drug substance therethrough when collapsing the container. However, such a membrane is difficult to manufacture as the reproducibility of the pores is poor. Also, the difference in length and diameter of the pore channel results in a considerable difference of pressure drop across this channel. This varying pressure drop will thus also lead to a variation of the quantity and droplet size dispersion of the drug being expelled. Another problem is the alignment of the movable membrane with pores over each unit container resulting in another source of uncertainty over the expelled amount of drug.

Indeed, the fabrication tolerance $\Delta$d of the pores, or outlet nozzles, is an essential factor in controlling and determining the amount, i.e. the volume of an expelled droplet. In fact, this volume V depends on $d^3$ ($V=1/6 * \pi d^3$), d being the diameter of the outlet nozzle. For example, if d=5 $\mu$m, and $\Delta$d=±0.5 $\mu$m, the droplet volume V may vary from 47.5 (d=4.5) to 87 (d=5.5) which is a variation of 83%, far too high for usual industry standards. The United States FDA (Food and Drug Administration) imposes a repeatability of ±20% for 90% of the droplets, and ±25% for the remaining 10%. Both the device according to WO 92/11050 and to U.S.Pat. No. 5,497,763 do not allow for such precision and repeatability.

Also, the pre-cited documents are silent about avoiding layers or areas of liquid drug forming on the outside surface of the nozzle array by well known capillary action and stiction. This is especially the case with devices where the same nozzle array is used several times, such as for example in the documents WO 92/11050 or Wo 90/01997. Such layers lead to the forming of liquid meniscus in front of the nozzles which are broken up by the piezo-activated spraying action but lead to a larger droplet size dispersion than without such layers.

The document U.S. Pat. No. 5,497,763 partially overcomes this problem by separating dosage containers and the porous membrane through which the drug is aerosolised. However, the solution does not allow for the precision and repeatability of the cone-shaped pores used and the precise control of the drug delivery, requiring a pressure to be applied additionally to the piezoelectric vibrating means to force the liquid out. Also, the piezoelectric vibrating means is not compensated for its non-linearities adding to uncontrolled factors affecting the delivery of targeted delivery.

It is, therefore, an object of the present invention to provide a liquid droplet spray device for an inhaler, as well as an inhaler itself, suitable for respiratory therapies which overcomes, at least partially, the inconveniences of the prior art and which allows for a true targeting of the impact of droplets thereby assuring a constant droplet size. In fact, this virtually constant physical size of the droplets, or mono-dispersion of the droplets allows for an exact determination of the volume of liquid released and deposited.

It is another object of the present invention to provide such a device which is simple, reliable to manufacture, small in size and low in cost.

Thus, the present invention concerns a liquid droplet spray device according to present claim 1 as well as a liquid droplet spray device assembly according to present claim 8. The present invention further concerns an inhaler according to claim 17 allowing for a predicted deposition, and to claim 21 comprising several inventive spray devices to obtain a highly reliable operating system for anaesthetics or critical medication nebulisation thanks to an operating redundancy of the spray devices.

Thanks to the specific structure of the dispersion or outlet nozzle of the spray device according to the present invention, i.e. thanks to the combination of a tapered cavity with a number of identically sized and toleranced straight non-tapered channels or distribution of such channels with different dimensions, it is possible to obtain a high precision, tightly toleranced output nozzle array resulting in a virtually mono-dispersive droplet size so that it is possible to determine with improved accuracy, compared to prior art devices, the place of impact, i.e. the deposition of the droplets on the different selected lung sections as well as the amount of substance that arrives there. Further, thanks to flow measurement and pressure supervision means which are preferably incorporated into the inventive spray generating device, it is also possible to conclude with precision on the delivered dose, and thanks to control means which are further preferably provided, it is possible to calculate a predicted deposition of the mono-dispersive droplets and to adapt to the type of medication and patient concerned. Thus, an efficient therapy may be performed. Further, thanks to the inventive spray device, only a minimal amount of liquid is used as the exact amount released can be predetermined with a high precision so that there is only a very small amount of waste and that the side-effects can be limited too.

Figure 5:
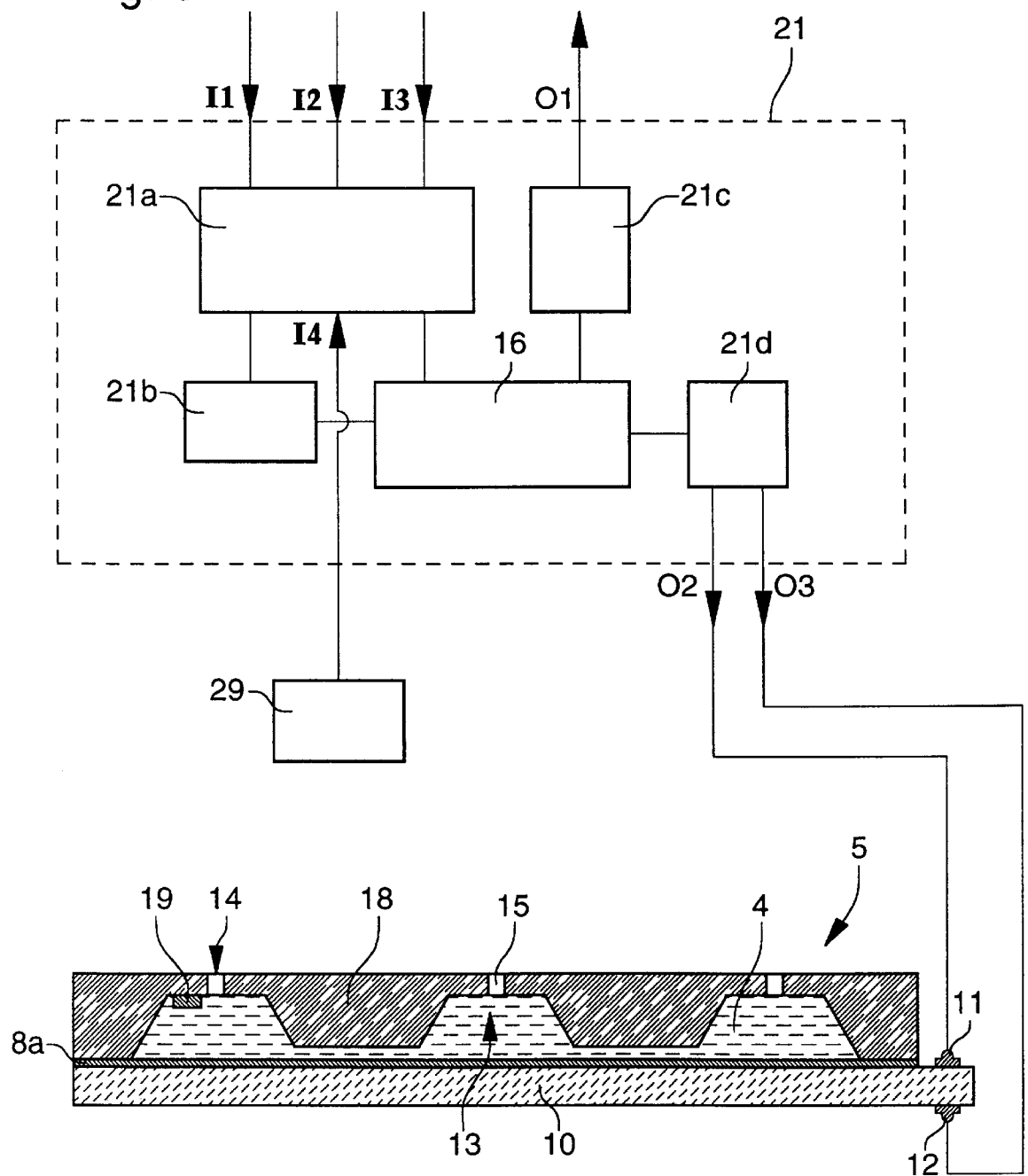
Figure 6:
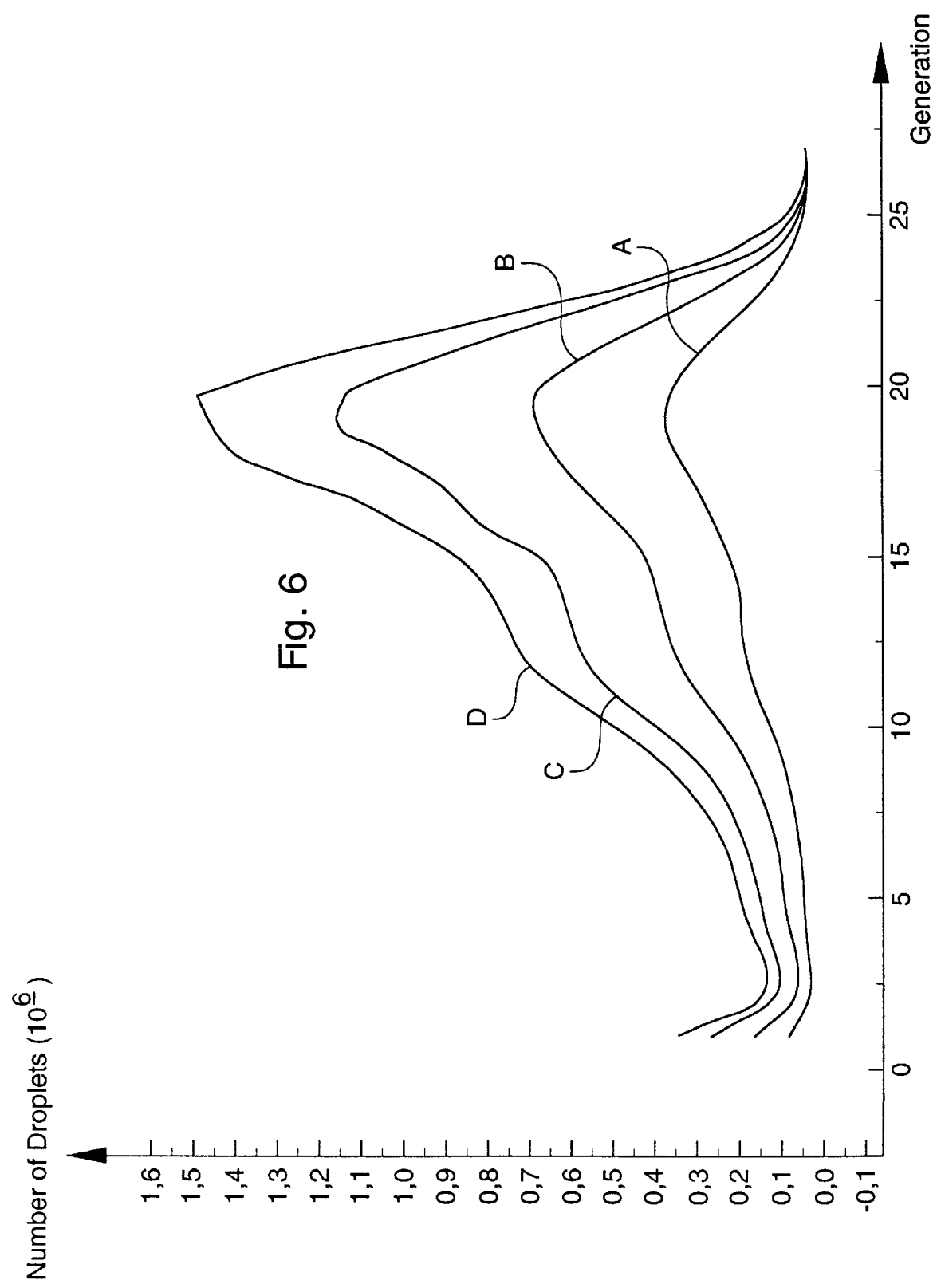

Other features and advantages of the liquid spray device according to the present invention will become clear from reading the following description which is given solely by way of a non-limitative example thereby referring to the attached drawings in which:

FIG. 1 shows a preferred embodiment of an inhaler suitable for respiratory therapies comprising a liquid droplet spray device according to the present invention, FIG. 2 is a schematic cross-section of a first embodiment of the liquid droplet spray device according to the present invention, FIG. 3 is a schematic cross-section of a second embodiment of the liquid droplet spray device according to the present invention, FIG. 4 is a schematic cross-section of a third embodiment of the liquid droplet spray device according to the present invention, FIG. 5 shows a schematic block diagram of the electronic circuitry used in the inhaler according to the present invention, and FIG. 6 is a graphic representation of the deposition of the number of droplets against the lung generation for a given flow rate and as a function of time.

Referring now to FIG. 1, an embodiment of an inhaler suitable for respiratory therapies is indicated by general reference 1. Inhaler 1 comprises a housing 2 having a magazine 28 which may comprise a reservoir 3 containing a liquid drug substance 4. Housing 2 is connected to a mouthpiece 6 in communication with the exterior of housing 2 to allow delivery of the drug to the patient by way of his mouth. Naturally, mouthpiece 6 may be replaced by a nasal piece, or may be fitted with a nasal adapter to allow the inhaler to deliver the drug through the nose of the patient instead of through his mouth. However, reference will be made throughout the present description to a mouthpiece only thereby meaning a mouthpiece or a nasal piece or a nasal adapter or a nebulising set with or without a face mask.

For ease of use, housing 2 may consist of two separable parts, upper part 2a and lower part 2b respectively, interconnected by hinges 26 and 27 or by other appropriate releasable securing means as described in more detail in the document EP 0 824 023. Lower housing part 2b has mounted therein magazine 28 which comprises at least one drug delivery system in the form of at least one liquid droplet spray device 5 each containing a space 9 (see FIG. 2) for storing liquid substance 4. Magazine 28 may further comprise a non volatile memory means 29 connected to electronic circuitry or means 21, and a portable power source 22, such as a lithium battery. Upper housing 2a may contain additional magazines as a reserve. Magazine 28 is rotatably mounted in lower housing part 2b about an axis 23 so that, upon rotation of magazine 28 about this axis 23, each spray device 5 is placed, in turn, in a delivery position with respect to mouthpiece 6. To this effect, the magazine may be caused to rotate about axis 23 by a stepper motor, not shown, controlled by electronic circuitry 21. Each spray device may comprise a sealant to maintain substance 4 within space 9 and which is peeled off when the spray device is aligned with mouthpiece 6. Such sealants are well known in the art and will not be explained in more detail here. However, it is also possible that there is only one spray device 5 which is re-filled whenever necessary from reservoir 3 by way of a micro-valve 17 controlling this filling.

Thus, reservoir 3 is connected to liquid spray device 5 which comprises space 9 containing a unit dose, such as 10 to 30 μl or another suitable small amount of drug substance 4. Liquid spray device 5 creates droplets of substance 4 by atomising the liquid substance as will be explained in more detail further on. The droplets are released into mouthpiece 6, or the nasal adapter or the nebulising set, which has an open end to be inserted into the mouth, or nose, of a person so that the droplets may enter his or her respiratory airway.

FIG. 2 shows in more detail the structure of the liquid droplet spray device 5 according to the present invention. Liquid substance 4 enters spray device 5 by way of e.g. a very low pressure or capillary action. Such very low input pressure is important to provide very low exit velocity of the aerosol which is consequently easily absorbed into the inhalation air stream, limiting medication deposition losses in the extrathoracic region. This can be achieved for example by way of at least one supply tube or needle 7 through which a liquid substance may be supplied from at least one reservoir 3 into spray device 5. However, this filling may also be piston or plunger activated, however with pressure reduction or performed by way of a pump or a micropump at very low pressure. This may be carried out as described in the document U.S. Pat. No. 5,462,839. As mentioned, a micro-valve 17 may be provided to isolate reservoir 3 from spray device 5. This valve 17 may be external to the spray device as is shown, but it can also be integrated into the substrate or be part of the micropump supplying the filling. Preferably, valve 17 is controlled by medication flow measurement means 19 which are provided and which may be incorporated in spray device 5 thus allowing precise dosage in conjunction with the valve. The reservoir 3 can be realised in a variety of forms so as to contain from several microliters to several millilitres. A non-volatile memory 29 may further be suitably arranged within this reservoir 3.

However, it should be noted that reservoir 3 need not be provided at all or that liquid spray device 5 itself can act as a reservoir. This can be the case for example when substances cannot stay in a container over an extended period of time or are to be mixed before atomisation of the mixed component, one substance being contained in reservoir 3 and the other in the pre-filled spray device 5. In any case, non-volatile memory 29 may contain information about a further provided vibrating means 10, which is explained in detail hereafter, and about identity and dosage of substance 4 or substances contained in reservoir 3 and in pre-filled liquid spray device 5. In another case, each liquid spray device 5 is pre-filled with the desired unit dose of a substance 4. Of course, when there is no separate reservoir 3, tube 7 is plugged to seal space 9, or even non-existant and no valve is needed. Thus space 9 is dimensioned such that it may contain the required amount corresponding to the desired unit dose, and a number of pre-filled spray devices 5 form magazine 28 such as described earlier.

Spray device 5 consists thus of a housing formed of a superposition of a first or top substrate 18 and a second or bottom substrate 8 into which a space 9 is etched for containing liquid substance 4. In the embodiment as shown in FIG. 2, bottom substrate 8 thus has a thinner middle section acting as a membrane as will be explained further on. Bottom substrate 8 may be made of glass, ceramics, silicon, high density polymer or the like. Top substrate 18 may consist of plastic, high density polymer, ceramics, metal or silicon or the like for its main body, and of silicon for its nozzle body as will be explained in more detail further on. The substrates 8 and 18 are attached to each other, for example by anodic or fusion bonding, so as to form and enclose space 9. Bottom substrate 8 may also be fitted upside down with respect to the manner shown in FIG. 2, so that the bottom of space 9 is flat, this allowing for a higher compression of the volume of space 9 and for a more compact spray device 5. Device 5 also comprises a piezo-resistive element acting as the aforementioned flow measurement means 19. This means 19 may be deposited on the inner surface of top substrate 18 or it may even be integrated into this top substrate and is located such that it may detect the flow of the droplets. For this reason, it is important that channels 15 and nozzles 14 are tightly sized and toleranced and have a defined, repeatable pressure drop.

A selective hydrophilic coating, such as an amorphous material such as $SiO_2$, may further be applied to provide a protective layer around the inside walls of space 9 and/or of cavities 13 which are located in top substrate 18 as is explained hereafter to avoid any contamination of substance 4 by the material of these walls and to improve wettability in certain parts. This may be carried out as described in the document EP-A-0 641 934. This hydrophilic coating which may be applied as a selective, patterned coating is advantageously coupled with a selective, patterned hydrophobic coating in certain areas of space 9, cavities 13 and on the outside of substrate 18. In order to maintain the protective aspect of these surfaces and at the same time to reduce the internal and external stiction due to capillary forces in space 9, and especially on the outside of substrate 18, a hard amorphous carbon film, e.g. a diamond-like carbon, is provided, preferably in a selective patterned manner in these areas. Such selective film coating also allows for a more complete emptying of space 9 due to reduced stiction. Such coating and its hydrophobic properties can be enhanced by fluorine plasma.

The present Applicant has found that such surface property specific coating influences and improves droplet size dispersion and provides an even better monodispersive pattern released by the spray device.

If substrate 18 is made, at least partially, of a polymer, then a polymer with very low surface energy is used advantageously in combination with the selectively patterned hydrophobic coating. If substrate 18 is made of a polymer, acrylic or e.g. a photosensitive epoxy including or not said selective hydrophobic coating, e.g. a diamond-like nano-composite or Teflon® coating, a silicon etched mask, using the deep silicon etching process described hereafter, is preferably used by providing the masks on the wafer used to obtain the top substrate to facilitate precise plasma etching, e.g. $O_2$ plasma or UV exposure of photosensitive materials, of the channels and of the output nozzles which are provided in the top substrate in said materials, as will be explained in more detail further on.

Device 5 preferably comprises a vibrating element 10, e.g. a piezoelectric element, attached to the exterior bottom surface of bottom substrate 8 in the vicinity of its thinner middle section to cause vibration of substance 4 in space 9 through the membrane part of substrate 8. However, this element may also be located separated from spray device 5 directly onto a PCB. This element may be glued to or deposited on the bottom surface of the spray device or on the PCB. Electrodes 11 and 12 are applied to piezoelectric element 10 and to bottom substrate 8 respectively. These electrodes may be spring-contacts which contact appropriate electrodes (not shown) connected to electronic means 21 when the spray device 5 is rotated into its delivery position. If the element is arranged on the PCB with or without intermediary elements, clamping means may be provided to bring the spray device into contact with the piezoelectric element 10 as will be explained in more detail furtheron with reference to FIG. 4. As may be readily understood, by assembling this piezoelectric element to the thinner middle section of the bottom substrate which itself is assembled in the upside down manner mentioned above, a very compact spray device may be obtained. In this case for example, the operating data relating to vibrating element 10 are contained in electronic circuitry 21 and non-volatile memory 29 contains only data relating to the identity and the dosage of the substance or substances to be delivered.

It has been observed that the droplets size is inversely proportional to the excitation frequency as of a particular primary frequency and pressure. Preferably, piezoelectric element 10 vibrates at that particular primary frequency which may be for example around 470 kHz. Of course other frequencies may be used if appropriate. Indeed, several embodiments have been satisfactorly tested by the Applicant at a frequency of 100 kHz and even of 30 kHz. It should be noted that the lower the frequency, the lower the power consumption, but the higher the number of outlet nozzles so as to obtain a desired liquid substance output. This vibration may be generated in a known manner e.g. by using a frequency oscillator.

Advantageously, a flexible heating surface, such as a captan film with heating element, not shown, can be suitably fitted on substrates 8 and 18, to heat the liquid substance, to e.g. around 37° C., by applying an electric current in an appropriate manner to this heating element. Of course, it is also possible to deposit a conductive material on the inner surface of bottom substrate 8, which thus corresponds to the bottom of space 9, to heat the liquid by applying a current to this conductive material.

Thanks to this heating, the influence of any temperature fluctuations on substance 4, and in particular on the particles which this substance contains, may be largely controlled. In fact, it is known that the dimensions of steroids which are commonly used in a drug substance vary with the temperature and become more soluble with a higher temperature, see for more details the article "Steroid/Cyclodextrin complexes for pulmonary delivery" by G. M. Worth, M. Thomas, S. J. Farr and G. Taylor; Proceed. Int'l Symp. Control. Rel. Bioact. Mater., 24 (1997), pages 747 & 748, Controlled Release Society Inc. Furthermore, thanks to this heating, humidity influences due to the environment in which the spray device operates may also be taken into account to ensure correct functioning.

Furthermore, such heating may contribute at the end of the atomisation cycle to evaporate any minute amount of liquid left in space 9, same as a continuation for a predetermined time of the actuating of the vibrating means after the inhalation cycle has ended.

Preferably, a temperature influence compensation of the frequency oscillator is also provided to ensure that the excitation frequency of piezoelectric element 10 may be controlled by an appropriate feedback control circuit, again to avoid differences in droplet size and to ensure correct operation under varying ambient conditions. In a preferred embodiment, these feedback control means or compensation means may comprise at least one polynomial processor in which non-linearity compensation factors, such as those due to the temperature, the humidity or other environmental factors are pre-stored in the nonvolatile memory device 29 such as e.g. an EEPROM, together with the corresponding medical device quality-controlled related data and medication identification and dosage instructions, as explained in more detail with FIG. 5.

Such an EEPROM or other memory device is preferably associated, in a modular fashion, with the reservoir, the valve etc., and the spray device, which might be disposable, according to the configuration, allowing to use the same power source 22 and electronic circuitry 21 for multiple diverse therapies. For example, an asthmatic or a diabetic person may use the same inhaler for two types of medication by exchanging the reservoir, the valve etc. and spray device module.

An example of the dimensions of the different parts of spray device 5 is given hereafter The height of space 9 is less than 400 μm, the top surface of bottom substrate 8 is etched away for about 200 μm for a spray device having a total top surface of about several square millimetres.

As mentioned above, in a preferred embodiment, top substrate 18 may be formed of two materials, plastic for the main body, and silicon for the nozzle body. This nozzle body corresponds to a centre part of top substrate 18 which comprises outlet nozzles 14 and accesses from space 9 to these outlet nozzles. Silicon is preferably used for this nozzle body as it may be micromachined to obtain a very high precision manufacturing, such a high precision and absence of leachable components being much more difficult to obtain with plastics or the like, for instance by using an UV exposure or a plasma etching treatment of various plastic material, but silicon is also more expensive than plastics. However, top substrate 18 may of course be made of only silicon or even of only plastics. Outlet nozzles 14 and accesses are formed in the nozzle body of the top substrate 18, so that the excited substance 4 may leave device 5 as a droplet spray. To this effect, this top substrate 18 is micromachined, for example in a well known anisotropic etching manner at several places to obtain tapered, cut-off pyramid-shaped cavities 13 which are for example about 200 to 400 μm deep. These cut-off pyramid shaped cavities can have a square or an elongated base and be of any number to provide the correct internal volume and flow characteristics for a particular substance 4. Each cavity 13 then has a top surface having a side length of about 100–200 μm. Within this top surface of each cavity 13 at least one output channel 15 is provided to connect cavity 13 to an outlet nozzle at the exterior of top substrate 18. This output channel is preferably micromachined using a rapid deep vertical anisotropic plasma etching of silicon, e.g. at room temperature or low temperature and advanced silicon etch solution process. The Applicant has developed techniques to machine these channels with a near vertical and smooth profile, thereby significantly reducing undercutting and maintaining tight control over tolerances. This provides for a precisely defined pressure drop, droplet size and flow behaviour across channel 15 for aqueous solutions and suspensions whereas the smooth surface is suited for medications carrying small solid articles, e.g. 1 to 3 μm, in suspensions. The same effect can be obtained proportionally with larger dimensions, e.g. with nozzles of 10 μm or larger.

Thus, at the outer end of each output channel 15 at least one output nozzle 14 is provided through which the excited liquid substance is ejected as a droplet spray. The used technology allows to etch extremely precise, deep channels having straight and smooth side-walls and being round or square with a very tight, repeatable tolerance and allows to etch areas around nozzles 14 as explained herebelow. The process between lithography and etching can be arranged so as to adapt the lithography mask to the desired diameter as a function of the process tolerances thus guaranteeing the uniform precision of the nozzles and of the droplets. In the present example, each output channel 15 is about 15 μm long and 5 μm wide with nozzle 14 having a maximum opening of around 5 μm. Dimensions as well as the number of nozzles may of course be readily modified depending on the amount of drug and on the corresponding droplet size to be ejected as will be explained in more detail here after. However, it should be noted that the length of this output channel 15 should not be too long to avoid a large pressure drop across this channel resulting in a change of the droplet size as ejected.

Preferably, a selective, patterned hard amorphous carbon film, e.g. diamond-like carbon, of for example 100 μm ($10^{-9}$ m) is deposited in various areas, notably inside all or part of cavity 13 and output channel 15, certain areas of space 9 and on all or part of the outside of substrate 18. Such coating further improves smoothness and lowers flow resistance in channel 15.

FIG. 3 shows a second embodiment of liquid spray device 5 in which vibrating element 10 and bottom substrate 8 are advantageously replaced by a single piezoelectric ceramic element 10 of an appropriate shape. The different parts which correspond to those of FIG. 2 have been indicated by the same reference numerals. A protective glass or a silicon-nitrate layer, referenced 8*a*, is deposited on this vibrating element 10 to isolate the latter from substance 4. This deposition avoids undesired leachables from the vibrating element 10 or its electrode into the drug substance. The selective, patterned hydrophilic or hydrophobic coating can be applied similar as to the previous embodiment.

FIG. 4 shows a third embodiment of liquid spray device 5 as described in the previous embodiments in which the vibrating element 10 does not form part of spray device 5 as such. Instead, this element 10 is arranged on a support, for example a PCB, indicated by reference P, which may further contain e.g. the electrodes, the power source and the electronic means 21 for the vibration generation and dosage control including a non-volatile memory for the functional parameters of the piezoelectric element 10. Liquid spray device 5 may then be brought into tight contact with piezoelectric element 10 using appropriate attachment means, e.g. by one or more clamping devices 10a, for attaching the spray device to the PCB. Together, this spray device and the PCB comprising the vibrating means, i.e. the piezoelectric element, form a liquid spray device assembly which functionally corresponds to the spray device of FIGS. 2 and 3. Clamping means 10a may be provided either as a separate element or may be formed integrated with the PCB to allow for a quick clamping of spray device 5. Such clamping means are well-known as such and may be readily conceived by a skilled person. Furthermore, the top substrate may be micromachined in such a way as to provide recessed areas around output nozzles 14 such as shown. Such top substrate 18a may of course also be used in the embodiments of FIGS. 2 or 3. Such recessed areas in combination with straight output channels 15 and tightly toleranced output nozzles 14 contribute to the monodispersive nature of the ejected spray by providing minimum stiction surface for the liquid 4 around output nozzles 14.

The ratios between the different individual dimensions, such as the internal volume height of space 9, the distance between the nozzles, the length of the membrane part of substrate 8 etc. result in factors such as compression ratio, stroke amplitude of the membrane etc. which together with the electronic parameters such as amplitude and frequency allow to adapt the inventive spray device to various liquid characteristics such as viscosity.

Thanks to the inventive arrangement of spray device 5, virtually mono-dispersive droplets are ejected which allow for a precise calculation of the amount of drug which will enter the various parts of the lungs. As the top surface of cavity 13 is much larger than the actual nozzle surface, it is thus possible to provide several outlet nozzles 14 on each cavity surface in order to eject more droplets simultaneously, and thus a larger amount of drug. Advantageously, several cavities 13 can also be combined to form a single elongated cut-off pyramid-shaped trench, and even several of these trenches may be combined in a suitable arrangement. An increased internal volume is then obtained which also has a lower impact risk for the excited liquid trying to leave the device. Furthermore, such an arrangement is easier to manufacture and is thus lower in cost.

The diameter of a droplet depends on the nozzle hole size for a given frequency of the vibration of the liquid substance and the inlet pressure. In the present example where a frequency of around 470 kHz is used, the droplet diameter has been found to be around 5 $\mu$m, the diameter of the hole of nozzle 14 is around 7 $\mu$m and the inlet pressure is a few millibar. One such a droplet thus contains a quantity of around 67 femtoliters ($10^{-15}$ l) so that as such the number of nozzles may be determined as a function of the amount to be ejected. In a practical case, the number of nozzles may vary from around 600 to about 1500.

Further, a frequency vibration adaptation may be provided. Indeed, the exact resonance frequency of the piezoelectric vibrating element varies from one piece to another and as a function of ambient conditions such as the temperature. In case the liquid droplet spray device is a disposable part of the inhaler containing the reservoir as described above, it is advantageous to further provide the aforementioned EEPROM memory device with parameters containing the exact resonance frequency of the vibrating piezoelectric element forming part of the liquid droplet spray device. Electronic means 21 are preferably arranged to detect and to correct mode and frequency range of a particular piezoelectric element, to read this information and to adapt the vibration frequency to be applied to the piezoelectric element accordingly so that the new device will continue to function correctly under varying environmental conditions such as ambient temperature.

Inhaler 1 further comprises control means 16 (see FIG. 5) for controlling the amount of droplets to be ejected. This amount depends on the amount of drug which is to reach the different parts of the lungs. Control means 16 which may form part of electronic circuitry 21, advantageously further comprise an inhalation flow sensor 7 located conveniently, in this example near mouthpiece 6. Such a flow sensor is know per se, see e.g. the aforementioned document WO 92/15353. In this document, the sensor is used to determine an operating range within which the inhaler, a pMDI or a piston-activated device, will be activated. In the present invention, the inhalation flow sensor 7a is used in conjunction with the medication flow measurement means 19 and/or a lung model, explained hereafter, implemented in electronic means 21 to effectively measure and control drug flow for every inhalation according to a lung model calculation which is explained below and in connection with temperature measurement to provide a flow and temperature controlled unit dose.

In a preferred embodiment, medication flow measurement means 19 are realised in the way of a differential pressure sensor allowing a more complete supervision of the spray device by not only measuring the flow, but which may also detect an empty reservoir 3 and or space 9 as well as a possible occlusion.

The present Applicant has used, and implemented in electronic circuitry, a model of the lungs and of their functioning and, through a great amount of experimentation the following has been observed. As is generally known, the lungs which have 23 generations may be separated in three different regions: the trachea (until the sixth generation), the centre region (until the 16th generation) and the alveoli. However, it has been observed that a certain droplet size is more suitable for effectively reaching the different regions. For example, a droplet having a size of around 3 to 5 $\mu$m will easier reach the alveoli region, but a droplet with a size of around 10 $\mu$m will reach the centre region, whereas a droplet size of around 16 $\mu$m assures that the droplets arrive at the trachea region.

Thanks to these observations, it is thus possible to determine which droplet size and dosage of a drug is to be used for a desired therapy and for a type of patient (infant, child or adult) and to design the inhaler according to the required dosage.

Furthermore, thanks to the lung model, a formula was established which takes into consideration the principal losses which occur of the amount of drug due to several 30 physical influences. Indeed, it has been found that the amount of drug to be ejected, referenced De, relates to the amount of drug deposited on the target region, referenced Dd, for a given inhalation flow rate according to the following deposition efficacy equation:

$$Dd = U*V*X*Y*Z*De \tag{1}$$

in which U is an initial loss factor which occurs in the mouth and throat according to the article "Intercomparison of experimental regional aerosol deposition data" by W. Stahlhofen, G. Rudolf and A. C. James, Journal of Aerosol medicine, volume 2, number 3, 1989, page 285 ff., V is a loss factor due to exhalation of the patient before the droplets have reached their target, and where X is a loss factor due to sedimentation, or gravity, of the drug, Y is a loss factor due to impact loss at a bifurcation of lung branches, and Z is a loss factor due to diffusion in the lungs. These parameters may be determined for various flow rates, droplet sizes and molecular weight of the substance, and deposition probability models can be calculated. Naturally, it is well known that such parameters vary greatly between neonates, children and adults, because of the difference in lung size and surface available for deposition. The same dosage can thus result in large variations of drug concentration on the deposition site depending on the type of patient. The target amount De can thus be adapted to the type of patient thanks to the lung model implemented in electronic means 21 of the present invention.

A signal processing and digital compensation circuitry including a polynomial processor has been realised by the present Applicant for control means 16, for storing and processing the non-linearities of the inhalation flow sensor 7, medication flow sensor 19 and piezoelectric element 10.

FIG. 5 shows an example of a block diagram of the electronic circuit means 21 and its relation to the different elements such as the mentioned compensation means controlled by this means 21. The electronic means 21 receives parameters containing information coming from the inhalation flow means 7 at input I1, from medication flow means 19 at input I2, from a temperature sensitive element (not shown) at input I3 and from EEPROM 29 incorporated in reservoir 3 at input I4. Electronic means 21 contains at least one polynomial processor unit 21a arranged to receive and to sequentially process these parameters, an EEPROM or other non-volatile memory 21b connected to a first input/output of processor 21a, control means 16 in the form of a microcontroller connected to the output of EEPROM 21b and to another input/output of processor 21a, a vibrating element frequency oscillator driving stage 21d connected to the output of microcontroller 16 to adapt the frequency to be applied to vibrating element 10, and thus forming the aforementioned compensation means, and a booster valve control means 21c adapted to control the position of an optionally available boosting means as explained below. As mentioned, an output O1 may be provided to adapt the position of a suitably arranged booster valve as explained in more detail furtheron. Two other outputs O2 and O3 connect the output of the vibrating element frequency oscillator driving stage 21d to the electrodes 11, 12 respectively for exciting piezoelectric element 10.

An additional circuit featuring rule-based control designed by the Applicant, see the European patent application No. 95 908 180.3, allows for programming drug dosage as a function of the patient (his age, height etc.) and of various control parameters, such as inhalation flow rate, ambient temperature, deposition set point, etc. The above application discloses a decision-making aid (1) for delivering at least one drug to a living being. The decision-making aid includes a fuzzy logic processor for processing at least one first data item (I1) relating to the living being of interest and at least one second data item (I2) relating to the drug. The decision-making aid provides an output representing a customized amount of said drug to the living being requiring the same. The mentioned circuitry for control means 16 can of course be implemented as a very low power ASIC or using a microcontroller using the same or a similar software program. In a preferred embodiment, the piezoelectric element frequency oscillator driving stage 21d is realised in high voltage (10 to more than 30 volts) CMOS technology.

FIG. 6 shows a graph indicating the amount of droplets deposited in a particular lung region of an adult at a given flow rate with time for a given monodispersive droplet size and ratio. In this example, the inhalation flow rate is 20 l/min, and the droplet size is 5 $\mu$m. The graph is shown for a specific vibration frequency and for a certain number of nozzles of the liquid spray device. In this example of the deposition representation, the number of nozzles is 50 whereas the vibration frequency is 100 kHz. It should be noted that this graph represents a theoretical situation based on the above-mentioned lung model so that the indicated deposition after the 23rd lung generation is of course to be ignored. The figure shows several graphs, each graph representing a given time elapsed after the start of the inhalation cycle. It may be seen from this graph that after a first given time, in this example after 300 ms which corresponds to graph A, a certain peak amount of droplets, around 250,000, have been deposited around the 18th and 20th lung generation. After 600 ms, graph B, more droplets have been deposited, around 600,000, but the peak deposition remains around the 18th to the 20th lung generation. After 1000 ms, graph C, around 1,200,000 droplets have been deposited, also in this peak deposition region, whereas after about 1.3 seconds, see graph D, almost 1,600,000 droplets are deposited there. It should further be noted that, according to this model, if the vibration frequency is increased to 400 kHz, i.e. 4 times as high, the number of droplets deposited will increase with a factor four, but the deposition distribution will remain substantially the same. Clearly, the lung model thus allows for a predicted deposition of droplets at certain lung regions depending on parameters which may be controlled by a skilled person Thus, from this FIG. 6 it is clear that a skilled person can determine, for a given inhalation flow rate, the total amount of drug to be released in order to obtain the desired amount at a desired region. Indeed, the droplet size may be determined by the specific structure, and as the droplets are mono-dispersive, the total amount released may be determined.

The amount of droplets to be ejected may be controlled by the control means 16 in accordance with equation 1 which may be pre-programmed into these control means 16. Thus, depending on the different dimensions of the inventive spray device, the amount of droplets to be ejected may be determined and the control means may thus interrupt the ejection when the amount ejected has reached the desired amount. This may be performed by including measurement means such as the medication flow measurement means 19 within the spray device so as to allow for a determination of the amount ejected. Such means are in principle well known in the field, see e.g. the already mentioned document WO 92/11050.

However, this and other known solutions are bulky and require a relatively large dead volume which is of a disadvantage for the effective delivery of such small doses of around 10 to 20 $\mu$l. In order to overcome such problems, the following advantageous variant is proposed for flow measurement means 19. Preferably, a piezoelectric resistor is deposited inside top substrate 18 or 18a at a suitable location near the exterior of spray device 5. It can be assumed that the pressure outside spray device 5 is close to ambient pressure. The innovation of this variant resides in combining the inhalation flow sensor mentioned above and this internal pressure sensor, which is the flow measurement means 19, to determine the differential pressure allowing to measure the drug flow. Indeed, in a known manner, the piezoelectric resistor may form part of half a resistor bridge to measure the pressure, whereas the ambient pressure or the pressure inside mouthpiece 6 is considered known so that a differential pressure calculation may be determined. As mentioned above, this flow measurement means 19 may be integrated within top substrate 18 or 18a.

In order to ensure that a certain amount of the liquid substance ejected is not exhaled after the inhalation cycle and enters the lungs as far or as deep as possible, also at the end of the exhalation cycle of a patient, boosting means, not shown, are further preferably provided which are placed between the outlet nozzles 14 and mouthpiece 6. Such boosting means may comprise a duct having a pressure-drop section through which the droplet spray passes. Pressure control means, e.g. in the form of a valve-opening, are then provided in the duct to allow to lower the resistance in the duct. In this way, at the end of the inhalation cycle such as detected by the inhalation flow sensor, the resistance is lowered by opening the valve so that extra speed is provided to the droplets which may then be pushed downwards into the deeper regions of the lungs. As can be seen in FIG. 6 too, after a certain length of time, e.g. 300 ms (graph A), a large amount of droplets does indeed arrive at the target region, but there are also a lot of droplets which do not descend very deeply, but merely stay around the 5th or 6th lung generation and which may thus, with time, escape back out with the exhalation of the patient. These boosting means compensate for such non-desired effect at the end of the inhalation cycle and thus consist in forcing down the droplet spray into the lungs. This has as result that the graphs represented in FIG. 6 will be shifted towards the right, i.e. more droplets will reach the deeper regions.

Thanks to the inventive inhaler and its liquid spray device, an accurate prediction of place of deposition and of quantity of the drug substance may be carried out, thus resulting in a deposition optimisation so that a more efficient therapy may be obtained than is the case for the mentioned prior art device.

The mentioned inhalation sensor may also be used, with suitable adaptation, as an exhalation flow sensor in order to train patients to retain their breath for a certain period of time to aid the retention of medication, or to minimise the above mentioned exhalation losses, but also to correlate the mentioned exhalation loss factor V.

Advantageously, the inventive spray device may be used in a highly reliable inhaler for critical medications which comprises to this effect at least two spray devices. As the flow measurement means 19 allow to detect plugging or blocking of nozzles and/or an empty reservoir as is mentioned here above, it is thus also possible to detect the operation of the spray device itself, i.e. if this spray device is still functioning. The inhaler may thus, if a spray device is considered to be inoperative, switch, via electronic means 21, to another spray device to maintain the intended drug flow. Appropriate adaption to the electronic and/or control means may be provided to this effect, as such means may be conceived readily by a skilled person, they will not be described in detail here. Thanks to this redundancy of spray devices, a continuous reliable operation of the inhaler is obtained.

Having described the preferred embodiments of this invention, it will now be apparent to one of skill in the art that other embodiments incorporating its concept may be used. It is felt, therefore, that this invention should not be limited to the disclosed embodiment, but rather should be limited only by the scope of the appended claims.

What is claimed is:

1. Liquid droplet spray device, comprising a substrate, a space within the substrate for containing a liquid substance an inlet channel for connecting a source of liquid with said space, an outlet structure comprising a tapered cavity, disposed in said space of said substrate and having a cut-off pyramid-shape with a top surface, at least one outlet and at least one output channel connecting said top surface of the tapered cavity to said at least one outlet, wherein said outlet and said output channel have a straight non-tapered shape, and a vibrating element disposed to vibrate liquid in said space and eject the liquid through the at least one outlet.

2. Liquid droplet spray device according to claim 1, wherein said substrate is formed of a superposition of a first or top substrate and a second or bottom substrate, said output channel and said outlet being formed in said top substrate and having straight side-walls obtained by a deep vertical anisotropic plasma etching of said top substrate.

3. Liquid droplet spray device according to claim 1, wherein said substrate is formed of a superposition of a top substrate and a bottom substrate, said output channel and said outlet being formed in said top substrate and having straight side-walls which have a near vertical profile obtained by UV exposure of photosensitive plastics or by plasma etching of plastics or other micromachining, using a silicon micromachined wafer for providing the mask for obtaining the top substrate and said outlet structure.

4. Liquid droplet spray device according to any one of claims 1 to 3, wherein said space and said outlet structure are delimited by areas which are covered on certain parts with a hydrophilic coating and/or on other parts with a hydrophobic coating.

5. Liquid droplet spray device according to claim 1, further comprising electronic means for exciting said vibrating element.

6. Liquid droplet spray device according to claim 5, further comprising compensation means for compensating temperature influences on said vibrating element.

7. Liquid droplet spray device according to claim 5, further comprising a non-volatile memory means associated with said vibrating means and being pre-stored with parameters containing the exact resonance frequency of said vibrating element and with compensation factors for adapting said vibrating means to varying ambient conditions.

8. Liquid droplet spray device according to claim 7, wherein said non-volatile memory means further contains data concerning one or more variables selected from the group consisting of type of medication, patient intended for usage of said medication, and the intended dosage.

9. Liquid droplet spray device according to claim 7 or 8, wherein said electronic means is arranged so as to identify information from said non-volatile memory means to accommodate the controlled administration of a mix of substances or of more than one type of substance.

10. Inhaler for delivering drugs or anaesthetics, comprising at least two liquid spray devices according to claim 9, wherein said flow measurement means allows to detect the plugging of one or more of said spray devices, inhaler comprising control means for switching the operation of a first of said at least two spray devices to a second of said at least spray devices when said first spray device is plugged in order to maintain the desired delivery.

11. Liquid droplet spray device assembly comprising:
a liquid droplet spray device according to any one of claims 1 to 3,
said vibrating element being arranged in the immediate vicinity of a bottom portion of said substrate of said liquid droplet spray device to act on said liquid when excited so as to cause vibration of the liquid in said space thereby generating said droplet spray, and
an attachment member ensuring that said vibrating element remains in the immediate vicinity of said bottom substrate.

12. Liquid droplet spray device according to claim 11, further comprising medication flow measurement means for measuring the droplet spray ejection.

13. Inhaler for delivering drugs or anaesthetics, comprising at least two liquid spray devices according to claim 12, wherein said flow measurement means allows to detect the plugging of one or more of said spray devices, inhaler comprising control means for switching the operation of a first of said at least two spray devices to a second of said at least two spray devices when said first spray device is plugged in order to maintain the desired delivery.

14. Liquid droplet spray device according to claim 12, further comprising control means for controlling the droplet spray deposition, said control means being arranged to determine the amount of droplets ejected.

15. Inhaler for delivering drugs or anaesthetics, comprising at least two liquid spray devices according to claim 14, wherein said flow measurement means allows to detect the plugging of one or more of said spray devices, inhaler comprising control means for switching the operation of a first of said at least two spray devices to a second of said at least two spray devices when said first spray device is plugged in order to maintain the desired delivery.

16. Liquid droplet spray device according to claim 14, wherein said flow measurement means are located within a top portion of said substrate near said at least one output channel.

17. Inhaler for delivering drugs or anaesthetics, comprising at least two liquid spray devices according to claim 16, wherein said flow measurement means allows to detect the plugging of one or more of said spray devices, inhaler comprising control means for switching the operation of a first of said at least two spray devices to a second of said at least two spray devices when said first spray device is plugged in order to maintain the desired delivery.

18. Liquid droplet spray device according to claim 14, wherein said electronic means and said control means control the vibration generation such that a single unit dose of said liquid is ejected from said device so that said liquid may be transferred onto a predetermined surface.

19. Inhaler suitable for respiratory therapies comprising a housing containing a liquid droplet spray device according to claim 1, and a mouthpiece which has an end arranged to be inserted into the mouth or nose of a person so that said droplet spray may enter the person's respiratory airway.

20. Inhaler according to claim 19, further comprising boosting means for providing an air flow boost to transport said droplet, and wherein said control means further comprises inhalation flow measuring means for measuring the inhalation flow and for controlling said air flow boost.

21. Inhaler according to claim 19 or 20 for delivering drugs or anaesthetics according to an individually predicted deposition of a corresponding droplet spray of a liquid substance or a mix of substances into a respiratory airway of a patient using a spray device, further comprising a frequency oscillator driving stage which is arranged to vibrate the liquid at a predetermined frequency to create a droplet spray having mono-dispersive droplets of a predetermined diameter, said electronic means being arranged to measure and control the amount of droplets so as to eject a predetermined target amount of droplets, and to determine said predetermined target amount of droplets ejected De depending on the desired amount of droplets which are to be deposited Dd in a certain lung region as a function of the inhalation flow rate and according to the following preprogrammed formula:

$$Dd=(U*V*X*Y*Z)De$$

wherein U and V are initial droplet loss factors which depends on the patient, and wherein X, Y and Z are predeterminable, physical parameters compounded in a lung model and a corresponding control algorithm and in which De is a target deposition dose set-point which depends on the patient and his or her lung capacity.

22. Inhaler according to claim 21, wherein a first fraction of the predicted deposition of the dose can be realised in a first inhalation at a given inhalation flow rate, and the remainder of the predicted deposition, if necessary, can be administered in one or more subsequent inhalations, each at a different inhalation flow rate.

23. Liquid droplet spray device according to claim 1, wherein said spray device further comprises means for heating said liquid.

24. Inhaler for delivering drugs or anaesthetic, comprising at least two liquid spray devices according to any one of the claims 23, 6, 7, 8, to 15, wherein said flow measurement means allows to detect the plugging of one or more of said spray devices, inhaler comprising control means for switching the operation of a first of said at least two spray devices to a second of said at least two spray devices when said first spray device is plugged in order to maintain the desired delivery.

25. A liquid droplet spray device according to claim 1, further comprising
a nozzle body comprising a silicon substrate,
wherein said outlet structure is disposed in said silicon substrate.

26. A liquid droplet spray device according to claim 25, wherein said at least one output channel and said at least one outlet have straight side-walls obtained by a deep vertical anisotropic plasma etching of said silicon substrate.

27. A liquid droplet spray device according to claim 25, wherein said at least one output channel and said at least one outlet have straight side-walls obtained by UV exposure of photosensitive plastics or by plasma etching of plastics or other micromachining, using a silicon micromachined wafer for providing the mask for obtaining the nozzle body.

* * * * *